United States Patent
Grzeskowiak

(10) Patent No.: US 10,024,464 B2
(45) Date of Patent: Jul. 17, 2018

(54) HIGH-PRESSURE TUBE COMPRISED OF A PLURALITY OF CO-EXTRUDED LAYERS

(71) Applicant: Raumedic AG, Helmbrechts (DE)

(72) Inventor: Jörg Grzeskowiak, Hof (DE)

(73) Assignee: Raumedic AG, Münchberg (DE)

( * ) Notice: Subject to any disclaimer, the term of this patent is extended or adjusted under 35 U.S.C. 154(b) by 773 days.

(21) Appl. No.: 14/506,556

(22) Filed: Oct. 3, 2014

(65) Prior Publication Data
US 2015/0107714 A1   Apr. 23, 2015

(30) Foreign Application Priority Data
Oct. 17, 2013 (DE) .......................... 10 2013 221 101

(51) Int. Cl.
  *F16L 9/12*    (2006.01)
  *A61L 29/12*   (2006.01)
  *F16L 11/04*   (2006.01)

(52) U.S. Cl.
  CPC ............... *F16L 9/12* (2013.01); *A61L 29/126* (2013.01); *F16L 11/04* (2013.01)

(58) Field of Classification Search
  CPC ... F16L 11/04; F16L 9/12; C08L 75/04; C08L 77/00; A61L 29/126
  USPC ................... 428/36.9, 36.91, 36.92; 138/153
  See application file for complete search history.

(56) References Cited

U.S. PATENT DOCUMENTS

| | | | |
|---|---|---|---|
| 4,385,635 A * | 5/1983 | Ruiz ................. | A61M 25/0045 600/435 |
| 5,624,617 A | 4/1997 | Sorabella et al. | |
| 5,658,263 A * | 8/1997 | Dang ................ | A61M 25/0041 604/264 |
| 6,520,952 B1 | 2/2003 | Jimenez | |
| 2005/0277910 A1 * | 12/2005 | Dolla ...................... | A61L 29/12 604/529 |
| 2005/0277970 A1 | 12/2005 | Dolla et al. | |
| 2008/0154239 A1 | 6/2008 | Gielenz et al. | |
| 2009/0017247 A1 | 1/2009 | Ballet et al. | |

FOREIGN PATENT DOCUMENTS

| | | |
|---|---|---|
| DE | 10 2006 062 187 | 6/2008 |
| EP | 1 272 238 | 8/2005 |
| EP | 1 204 436 | 4/2008 |
| EP | 1 501 562 | 5/2011 |
| WO | 96/20741 | 7/1996 |
| WO | 2005/056097 | 6/2005 |
| WO | 2010078102 | 7/2010 |

* cited by examiner

*Primary Examiner* — Yan Lan
(74) *Attorney, Agent, or Firm* — Boyle Fredrickson S.C.

(57) ABSTRACT

A high-pressure tube comprises several co-extruded layers which include a reinforcing inner layer. Said reinforcing inner layer exhibits a mixture of a block copolymer and a homopolymer. As a result, a high-pressure tube is obtained the bending stiffness of which is reduced.

7 Claims, 1 Drawing Sheet

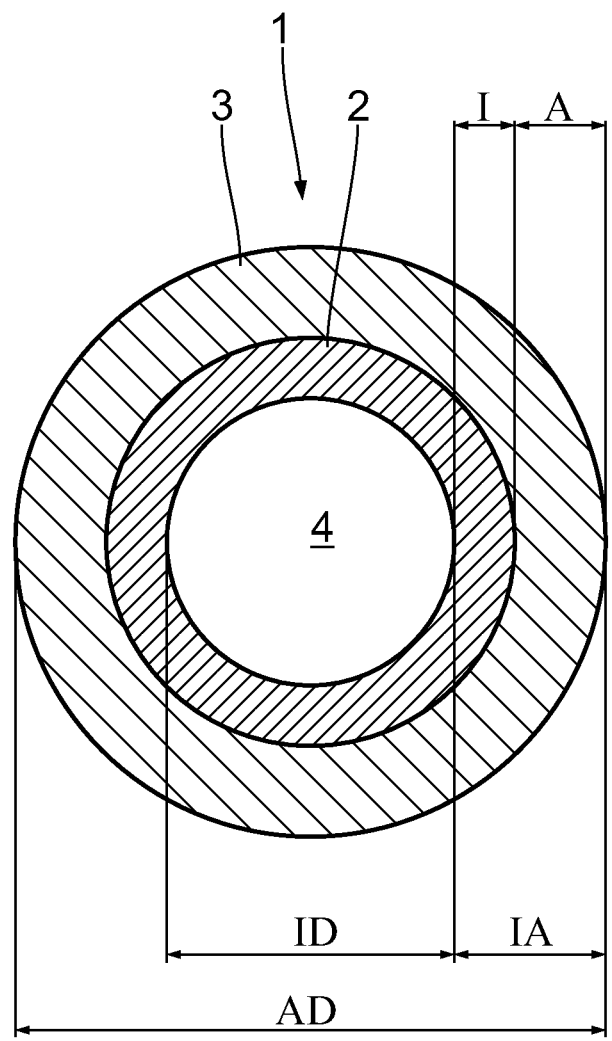

HIGH-PRESSURE TUBE COMPRISED OF A PLURALITY OF CO-EXTRUDED LAYERS

CROSS-REFERENCES TO RELATED APPLICATIONS

This application claims the priority of Patent Application Serial No. DE 10 2013 221 101.5, filed on 17 Oct. 2013, pursuant to 35 U.S.C. 119(a)-(d), the content of which is incorporated herein by reference in its entirety as if fully set forth herein.

FIELD OF THE INVENTION

The invention relates to a high-pressure tube comprising several co-extruded layers, in particular for medical use.

BACKGROUND OF THE INVENTION

A high-pressure tube for use in angiography is for instance known from EP 1 272 238 B1 and from EP 1 204 436 B1. Furthermore, high-pressure tubes are known which are configured as co-extruded tubes having a high bending stiffness on the one hand or as reinforced catheter tubes having a low bending stiffness on the other. Reinforced tubes, in other words fiber-reinforced tubes, are expensive to produce. US 2009/0 017 247 A1 describes a compressed-air hose made of polyamide, in particular for use as a brake hose. U.S. Pat. No. 5,624,617 describes a method for producing a guiding catheter. EP 1 501 562 B1 describes a catheter tube. U.S. Pat. No. 6,520,952 B1 describes a ceramic-reinforced catheter. DE 10 2006 062 187 A1 describes a catheter pipe element. WO 2010/078 102 A1 describes a high-pressure infusion catheter.

SUMMARY OF THE INVENTION

An object of the present invention is to further develop a high-pressure tube comprising several co-extruded layers in such a way as to reduce the bending stiffness thereof.

This object is achieved according to the invention by a high-pressure tube comprising several co-extruded layers, wherein one of the co-extruded layers is configured as a reinforcing inner layer, wherein the reinforcing inner layer exhibits a mixture of a block copolymer and a homopolymer with a mixing ratio of 60 to 90 parts of the block copolymer and 40 to 10 parts of the homopolymer.

It was found according to the invention that when using a mixture of a block copolymer and a homopolymer in order to produce the reinforcing inner layer, the bending stiffness of the high-pressure tube may be reduced significantly. A high-pressure tube of this type, which for instance needs to be able to withstand a burst pressure in the range of 80 bar, is used in angiography.

In this manner, an inner one of the co-extruded layers is configured in such a way as to ensure a high-pressure resistance. An outer one of the co-extruded layers is made of a material that is particularly bio-compatible. The tube may also have more than two co-extruded layers, for instance three, four or even more co-extruded layers.

The mixing ratio of 60 to 90 parts of the block copolymer and 40 to 10 parts of the homopolymer results in a bending stiffness of the inner layer—and therefore of the entire tube—that is greatly reduced according to requirements, wherein a sufficient high-pressure resistance is maintained despite the low homopolymer portion. The mixing ratio may for instance amount to 60:40, 65:35, 70:30, 75:25, 80:20, 85:15 or even 90:10.

The entire high-pressure tube is in particular made of bio-compatible materials.

A block copolymer configured as a polyether block amide having a Shore hardness in the range of between 60 D and 66 D and a homopolymer configured as a polyamide having a Shore hardness in the range of between 69 D to 75 D, turned out to be particularly suitable material components for the reinforcing inner layer.

An outer layer configured as a coextruded polyurethane layer having a Shore hardness of 70 A to 76 A also turned out to be particularly suitable for the tube. It is conceivable as well to use another material than polyurethane in order to produce the outer layer. The outer layer may be made of a material that has a lower bending stiffness than the inner layer and may have a Shore hardness of 75 A.

A layer thickness ratio of a layer thickness I of the inner layer to a layer thickness A of the outer layer such that 10%<I/A<65% ensures an advantageous distribution of the functions, e.g. high-pressure reliance" and "reduced stiffness", among the outer layer on the one hand and the inner layer on the other. The comparatively low layer thickness of the inner layer allows the bending stiffness to be reduced even more. It turned out that a relatively low layer thickness of the inner layer is sufficient to withstand a burst pressure predefined for a high-pressure tube. The layer thickness ratio I/A may amount to no more than 60%, to no more than 55% or even to no more than 50% and may even be lower, for instance no more than 45% or no more than 40%.

A bending stiffness lower than 3000 mN results in a tube that is flexible enough to ensure that a patient will hardly feel it even if he/she is moving. Also, this makes it easier for a doctor or a nurse to insert the tube.

An exemplary embodiment of the invention will hereinafter be explained in more detail with reference to the drawings.

BRIEF DESCRIPTION OF THE DRAWINGS

The only FIG. 1 shows a cross-sectional view through an embodiment of a high-pressure tube.

DESCRIPTION OF THE PREFERRED EMBODIMENT

A high-pressure tube has several co-extruded layers. In FIG. 1, the tube 1 is shown to include two layers. The inner co-extruded layer is configured as a reinforcing inner layer 2. The outer co-extruded layer, in other words the outer layer 3, is configured as a polyurethane layer.

The inner layer 2 shows a mixture of a block copolymer and a homopolymer.

The block copolymer is a polyether block amide. The block copolymer has a Shore hardness of 60 D to 66 D. In the polymer mixture of the inner layer, the block copolymer is a component which reduces the bending stiffness.

The bending stiffness is reduced by polyether portions of the polyether block amide.

The homopolymer of the inner layer 2 is a polyamide, namely pure PA11. The homopolymer has a Shore hardness of 69 D to 75 D.

The homopolymer ensures a pressure resistance of the tube 1.

The tube 1 is pressure-resistant up to a burst pressure of 83 bar. The high-pressure tube 1 is able to withstand a burst pressure of even more than 90 bar and in particular of 95 bar.

The polymer mixture of the inner layer 2 is formed by a mixing ratio of 60 to 90 parts of a block copolymer on the one hand and 40 to 10 parts of a homopolymer on the other.

The outer layer 3 has a Shore hardness of 70 A to 76 A.

The tube 1 has a total outer diameter AD in the range of between 3.61 mm and 3.75 mm. The illustrated tube 1 has an outer diameter AD of 3.68 mm.

The outer diameter AD is at the same time the outer diameter of the outer layer 3.

A free lumen 4 of the tube 1 has a diameter ID in the range of between 1.78 mm and 1.88 mm. The illustrated embodiment has an inner diameter of 1.83 mm.

The diameter ID is at the same time the inner diameter of the inner layer 2. A common layer thickness IA of the co-extruded layers 2, 3 of the tube 1 is in the range of between 0.865 mm and 1.43 mm. The illustrated embodiment has a total layer thickness IA of 0.925 mm.

The inner layer 2 has a layer thickness 1 in the range of between 0.28 mm and 0.33 mm. The illustrated embodiment has a layer thickness I of the inner layer 2 of 0.305 mm. The outer layer 3 has a layer thickness A in the range of between 0.535 mm and 1.15 mm. The illustrated embodiment has a layer thickness A of the outer layer 3 of 0.62 mm.

An I/A ratio of the layer thickness I of the inner layer 2 to the layer thickness A of the outer layer 3 is in the range of between 25% and 65%. The I/A ratio may amount to no more than 60%, to no more than 55% or even to no more than 50%. The I/A ratio may even be lower, for instance amounting to no more than 45% or no more than 40%. In order to ensure resistance to a burst pressure of 83 bar, the I/A ratio amounts to at least 25%.

The I/A ratio may however even be lower, for instance amounting to 10%.

The tube 1 has a bending stiffness which is lower than 3000 mN. This bending stiffness is determined by means of a bending length of the tube 1 of 20.0 mm. The tube 1 is bent at a bending speed of 6° per second up to a maximum bending angle of 30°. The force value that represents the bending stiffness is measured after a period of 2 seconds in which the tube 1 is held in this position, i.e. at said bending angle of 30°.

The illustrated and described embodiment has a bending stiffness which is even lower than 2500 mN, and which is even lower than 2200 mN.

What is claimed is:

1. A tube comprising a plurality of co-extruded layers with one of the layers comprising a reinforcing inner layer formed of a mixture of a block copolymer and a homopolymer and having a mixing ratio of between 60 and 90 parts of the block copolymer and between 10 and 40 parts of the homopolymer, and another one of the layers is disposed outwardly of the reinforcing inner layer and is formed of a polyurethane, wherein the polyurethane layer defines an outer layer of the tube and has a lower bending stiffness than the reinforcing inner layer, wherein the polyurethane layer has a Shore hardness of between 70 A and 76 A.

2. The tube according to claim 1, wherein the block copolymer comprises a polyether block amide.

3. The tube according to claim 1, wherein the homopolymer comprises a polyamide.

4. The tube according to claim 1, wherein the homopolymer has a Shore hardness in the range of between 69 D and 75 D.

5. The tube according to claim 1, wherein the tube has a bending stiffness of less than 3000 mN.

6. The tube according to claim 1 wherein the inner reinforcing layer has a thickness, I, the outer layer has a thickness, A, and the tube has a ratio of I/A of between 10% and 65%.

7. The tube according to claim 1, wherein the tube is configured to withstand a burst pressure of at least 90 bar.

* * * * *